US00PP11344P

United States Patent [19]

Pieters

[11] Patent Number: Plant 11,344

[45] Date of Patent: Apr. 11, 2000

[54] CHRYSANTHEMUM PLANT NAMED 'GEDI VL8'

[76] Inventor: Dirk Pieters, Schierveldestraat 3A, Oosnieuwkerke, 8840 Staden, Belgium

[21] Appl. No.: 09/148,799

[22] Filed: Sep. 4, 1998

[51] Int. Cl.[7] ..... A01H 5/00

[52] U.S. Cl. ..... Plt./290

[58] Field of Search ..... Plt./290, 287, 293

*Primary Examiner*—Howard J. Locker

*Attorney, Agent, or Firm*—Christie, Parker & Hale, LLP

[57] ABSTRACT

A new variety of Chrysanthemum producing large, dark bronze decorative type flowers.

1 Drawing Sheet

BACKGROUND OF THE INVENTION

The present invention is directed to a new and distinct variety of chrysanthemum botanically classified as *Dendranthema morifolium*. The varietal denomination of the new chrysanthemum is 'GEDI VL8'.

The new variety is a cross of the variety 'Sapiro' as female parent and the variety 'Cobra' (U.S. Plant Pat. No. 10,219) as male parent. The new variety has been asexually reproduced by vegetative cuttings in Ventura County, Calif. and the distinguishing characteristics are retained through successive generations of asexual reproduction.

SUMMARY OF THE INVENTION

'GEDI VL8' is a Chrysanthemum plant variety that produces large dark bronze decorative-type flowers on a mounding, non-brittle herbaceous perennial plant suitable for garden use.

COMPARISON WITH PARENTS

The new variety differs from its female parent in having larger flowers with more ray florets and from its male parent in having a dark bronze, decorative-type flower whereas 'Cobra' produces a light bronze daisy-type flower.

BRIEF DESCRIPTION OF ILLUSTRATION

The accompanying photograph shows a typical specimen of the new variety with colors being as nearly true as possible with illustrations of this type.

DESCRIPTION OF THE PLANT

The following description of the new variety is of specimens grown in a greenhouse in Ventura County, Calif. in the month of April. 'GEDI VL8' has not been observed under all possible environmental conditions. The phenotype may vary with variations in the environment such as temperature, light intensity, day length and cultural conditions. The color designations herein are from The Royal Horticultural Society Colour Chart except where general terms are used.

To produce a commercial product the plants may be pinched once about ten days after planting, with center bud removed. No growth regulator was used with plants described. Longevity of individual blooms of 'GEDI VL8' is about 25 days with a plant response time of about 6.5 weeks. Desirable growing conditions include average night temperatures of about 62°–64° F. and day temperatures of about 75°–80° F. Natural season response in Western Coastal conditions is about the beginning of September.

Plant:

*Habit.*—Herbaceous perennial, mounding plant form.
*Height.*—20 cm.
*Number of breaks from pinch.*—About 3 to 4.
*Length of lateral branches.*—About 16 cm.
*Stem color.*—Near 138B.

Foliage:

*Leaf arrangement.*—Alternate.
*Number of leaves per lateral branch.*—About 15 fully expanded leaves.
*Leaf size.*—Length: About 5.6 cm. Width: About 3.1 cm.
*Leaf shape.*—Ovate.
*Attachment.*—Petioled.
*Leaf apex.*—Obtuse.
*Base.*—Truncate.
*Margin.*—Deeply palmately lobed.
*Aspect.*—Slightly undulating.
*Surface.*—Top: Pubescent. Bottom: Pubescent.
*Venation.*—Mid veins prominent on underside. Color: Underside: Near 144B. Upperside: Near 138B.
*Petiole.*—Length: About 1.6 cm. Color: Near 137D.
*Color.*—Mature leaf: Top: Near 137B. Bottom: Near 138A. Young leaf: Top: Near 137B. Bottom: Near 138A.

Bloom:

*Inflorescence form.*—Cyme.
*Bloom form.*—Decorative.
*Number of blooms per branch.*—Avg. about 8.
*Diameter of fully expanded bloom.*—About 5.5 cm.
*Depth of fully expanded bloom.*—About 3 cm.
*Sepal number.*—About 25. Color: Near 137B.
*Peduncle.*—Length: About 5 cm. Habit: Slightly curved. Surface: Highly pubescent. Color: Near 138B.
*Flower bud* (*when just showing color*).—Color: Near 178C. Diameter: About 0.9 cm. Height: About 0.6 cm.
*Ray florets.*—Number per flower: About 205. Texture: Matte. Shape: Oblanceolate. Apex: Obtuse. Base: Tapered. Margin: Entire. Aspect: Reflexed down. Length: About 2.2 cm. Width: About 0.7 cm.
*Disc florets.*—Number per flower: About 8. Texture: Shiny. Shape: Cylindrical. Margin: Entire. Length: About 0.5 cm. Width: About 0.1 cm.
*Fragrance.*—Moderate musky scent.

Flower color:

*General flower coloration.*—Red/Bronze decorative with darker center.
*Ray florets, top side.*—Immature: Near 34B. Mature: Near 172C. Fading: Near 172D.

*Ray floret, under side.*—Immature: Near 168D. Mature: Near 163C. Fading: Near 163D.

*Disc florets.*—Immature: Near 154A. Mature: Near 2A. Fading: Near 7A.

*Changes as the flower age.*—Older ray florets become lighter in color.

Reproductive organs:

*Ray florets.*—Pistillate. Stigma shape: 2 branched. Stigma color: Near 7C. Style length: About 0.5 cm. Style color: Near 1C.

*Disc florets.*—Stigma shape: Linear. Stigma color: Near 7A. Style Length: About 0.4 cm. Style color: Near 4D. Stamen number: About 5. Anther length: About 0.2 cm. Pollen color: Near 17C. Pollen quantity: Moderate.

What is claimed is:

1. A new and distinct Chrysanthemum plant of the variety substantially as herein shown and described.

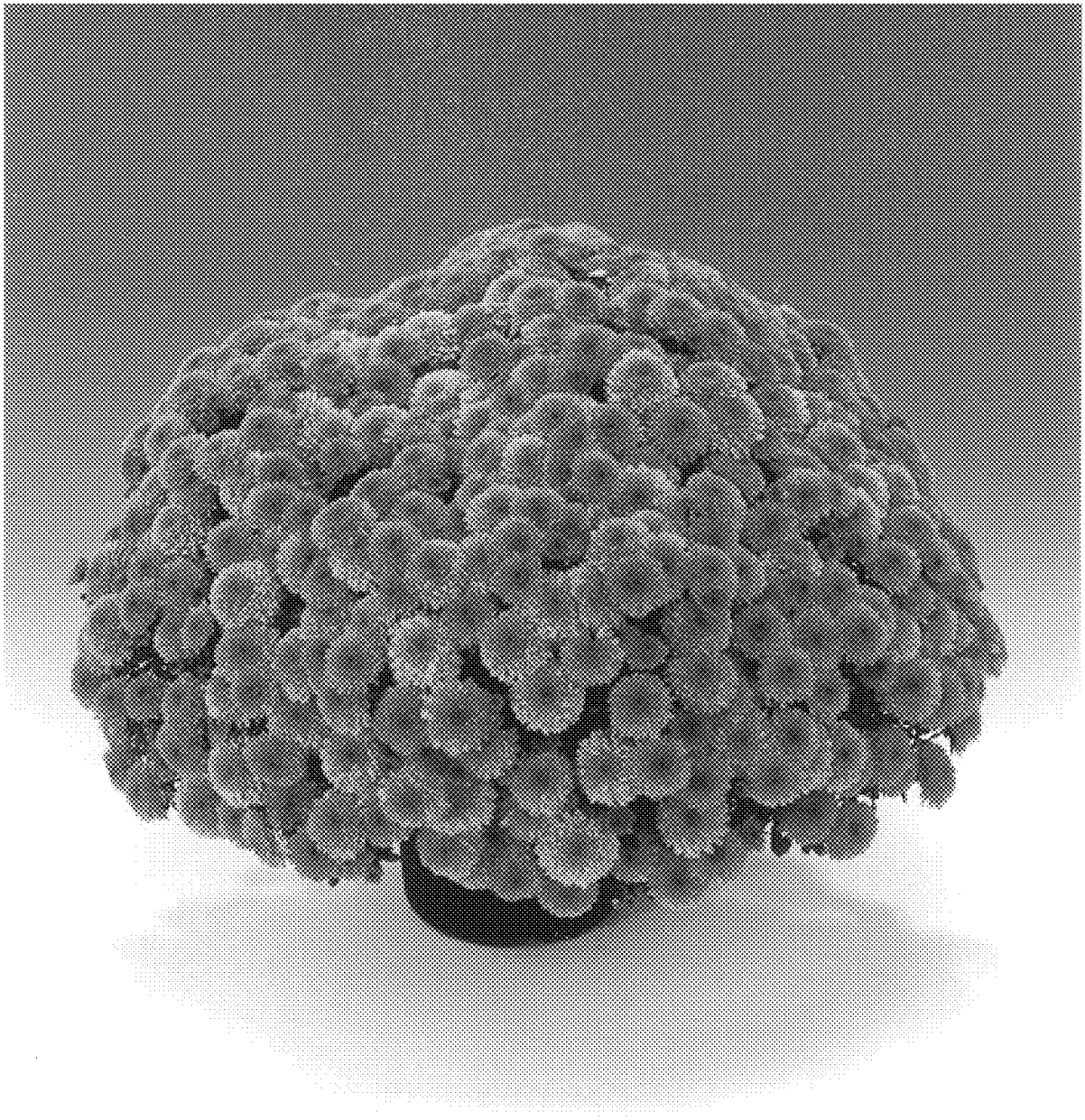

* * * * *